United States Patent [19]

Lee

[11] Patent Number: 4,664,128

[45] Date of Patent: May 12, 1987

[54] SINGLE-HAND CONTROLLED ASPIRATION DEVICE

[75] Inventor: Peter F. Lee, Edina, Minn.

[73] Assignee: Peter F. Lee, Inc, Edina, Minn.

[21] Appl. No.: 789,487

[22] Filed: Oct. 21, 1985

Related U.S. Application Data

[63] Continuation-in-part of Ser. No. 562,272, Dec. 16, 1983.

[51] Int. Cl.⁴ .................................... A61B 10/00
[52] U.S. Cl. ................................. 128/753; 128/763; 604/187; 604/227
[58] Field of Search .................... 128/762–765, 128/753; 604/218, 227, 187

[56] References Cited

U.S. PATENT DOCUMENTS

| | | | |
|---|---|---|---|
| 819,330 | 5/1906 | Ycaza | 604/218 |
| 2,198,666 | 9/1936 | Gruskin | 604/117 |
| 2,550,394 | 12/1948 | Young et al. | 604/218 |
| 2,660,342 | 4/1949 | Ruf | 604/211 |
| 2,705,494 | 10/1953 | Broadwin | 604/210 |
| 2,854,975 | 8/1958 | Cohen | 604/227 |
| 3,366,103 | 1/1968 | Keller | 128/764 |
| 4,354,507 | 10/1982 | Raitto | 604/222 |
| 4,484,915 | 11/1984 | Tartaglia | 604/227 |

Primary Examiner—Kyle L. Howell
Assistant Examiner—Randy Citrin
Attorney, Agent, or Firm—Merchant, Gould, Smith, Edell, Welter & Schmidt

[57] ABSTRACT

A disposable, single-hand controlled aspirating device for medical aspirating activities such as subcutaneous biopsy of fluid, soft tissue and bone marrow is provided. The aspirating device includes a syringe barrel, a plunger operative in the barrel, a finger grip member surrounding the exterior wall of the barrel that includes a collar portion engaging the exterior wall of the barrel and flange portions extending outwardly from the exterior wall of the barrel a distance sufficient to provide support for a user's fingers during aspiration procedures, and a spring surrounding the plunger portion external to the barrel for biasing the plunger outwardly from the barrel after the plunger has been advanced in the barrel toward the distal end thereof.

8 Claims, 7 Drawing Figures

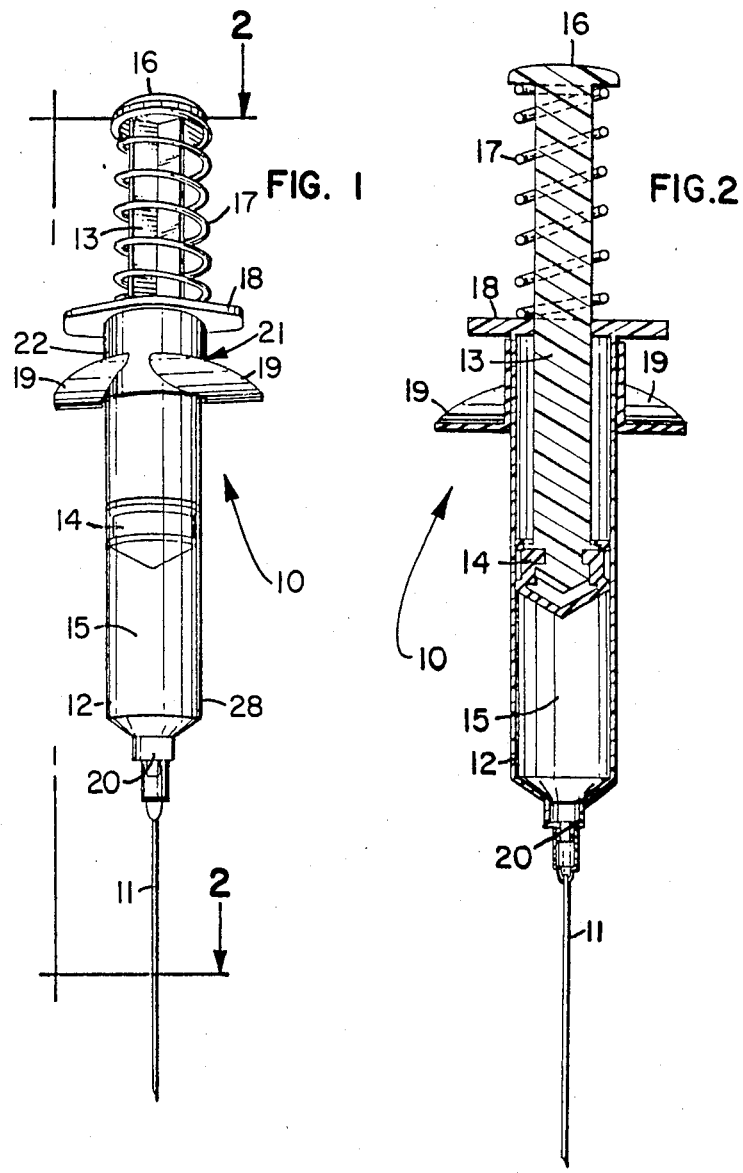

SINGLE-HAND CONTROLLED ASPIRATION DEVICE

CROSS-REFERENCE TO RELATED APPLICATION

This application is a continuation-in-part of copending application Ser. No. 562,272, filed Dec. 16, 1983.

TECHNICAL FIELD

The present invention relates generally to an aspirating device for use in medically-related aspirating procedures. More particularly, the aspirating device proprovides a sturdy and safe construction which is adapted for limited reuse or disposal after a single use. The aspirating device is similar to a medical hypodermic syringe and can be controlled by a single-hand during various biopsy procedures, such as biopsies of fluid, severing soft tissue samples and assisting in bone marrow biopsies.

BACKGROUND OF THE INVENTION

In medical applications an aspiration device is one which applies suction or partial vacuum to draw a fluid or sample into a syringe or into an attached needle lumen. Such devices are particularly useful for aspirating fluid and blood, and for securing soft tissue samples from the thyroid, liver, kidney and spleen, as well as from neoplastic and non-neoplastic pulmonary lesions, hepatic tumors, carcinomas of the breast, and palpable subcutaneous masses and nodes for histologic and cytologic examination.

At the present time, biopsy specimens are obtained by surgical excision or by needle biopsy. In the latter, soft tissue and aspirated specimens are obtained by any of several techniques, all of which involve applying negative pressure to the needle to obtain or assist in severing the specimen. Since most biopsies are performed by one person, certain device limitations have brought about procedural disadvantages with prior art techniques. These disadvantages are eliminated when using the device of the present invention.

The simplest and most widely used prior art aspirating device is a conventional, plastic hypodermic syringe of the type having a hollow needle opening into a syringe barrel and a plunger for varying the volume and pressure inside the syringe barrel. In use, negative pressure is applied by drawing back on the plunger. This requires two hands, one to hold the syringe barrel and one to withdraw the plunger.

The main disadvantage to using a conventional syringe as an aspirating device to assist in biopsy, is a necessity to have one hand free to do something other than operate the device. For example, when doing fine needle aspiration of a nodule, it is necessary to secure or immobilize the mass being sampled. This is usually done with two fingers of one hand, while making multiple sticks with the needle and at the same time applying intermittent or controlled suction with the other hand. Other procedures, such as biopsy of the liver or kidneys, are preferably done with the suction applied just prior to retracting the needle from the organ. When performed by one person, the procedure becomes a slow and somewhat cumbersome two-handed technique.

In fluoroscopic, ultrasound or CT scan aided biopsy, it is often necessary for a second person to assist with the procedure. This is sometimes accomplished by the addition of a flexible tube connecting the needle to the syringe barrel. The purpose of the tube extension is to allow one person to apply vacuum while the other controls the positioning of the needle for biopsy. Having suction applied by someone other than the person controlling the needle does not lend this approach to the general field of fine needle aspiration biopsy since the person applying the suction cannot easily determine when to apply it. In addition, this two-person approach not only adds to the professional component cost of the procedure, but it is also technically less effective since it generally requires more time than other procedures.

Prior medical aspiration devices suffer disadvantages of being structurally complicated and cumbersome thereby precluding convenient single-hand use. (See for example U.S. Pat. No. 3,819,091, issued to Hollender, June 25, 1974; U.S. Pat. No. 2,863,452 issued to Ogle, Dec. 9, 1958; and U.S. Pat. No. 2,472,116 issued to Maynes, June 7, 1949.

BRIEF DESCRIPTION OF THE INVENTION

The present invention is an improved aspirating device similar to a medical hypodermic syringe. Particularly, the present invention provides a plastic disposable aspirating device including a syringe barrel having a proximal end and a distal end. The distal end is provided with a hub and an opening through the hub. The hub is designed for attachment of a needle thereto, thereby providing for fluid communication between the syringe barrel of the device and the needle. A plunger is positioned in the barrel for changing the volume and pressure inside the barrel, thereby providing the necessary partial vacuum or negative pressure for aspiration as well as the positive pressure needed for expulsion of fluid. A relatively stiff spring surrounds the portion of the plunger positioned outside of the barrel extending along and around the plunger portion exterior to the syringe barrel. The spring biases the plunger outwardly from the barrel when the plunger is advanced in the interior space of the barrel. The aspirating device also includes a finger grip member along the exterior wall of the barrel substantially adjacent the proximal end thereof. The hub connecting the needle to the barrel can be of transparent plastic, as preferably is the barrel itself.

Among the purposes of the device is to provide an improved method for various biopsy procedures, including soft tissue biopsies and fine needle aspirations as well as obtaining bone marrow biopsy specimens.

The device of the present invention requires only one hand to be operated effectively. The other hand is then free for palpation or other functions common during biopsy procedures. By varying the times at which the gripping pressure is eased, suction may be readily applied as desired while the needle is being inserted, while the needle is in the tissue to be sampled, or while the needle is being retracted.

In use, the plunger is forced into the barrel by the user's hand as it grips the finger grip member with the palm of the hand resting against the exterior end of the plunger. Forcing the plunger into the barrel in turn compresses the spring surrounding the plunger. The amount or number of cubic centimeters of compression determines the total amount of partial vacuum or negative pressure (i.e. aspirating force) available within the syringe barrel upon relaxation of the tension applied by the user on the plunger.

The present invention solves deficiencies found in the prior art: the device is a self-contained aspirating device, eliminating the extra size associated with a syringe requiring the attachment of a separate device. As a result, the distance from the patient may be optimized. Biopsy is more efficiently performed by a single person and the technique easily learned. In soft tissue biopsy procedures, flushing the needle, advancing for biopsy and controlled application of suction can all be done with one hand. In fine needle aspiration procedures the operator can control the application and cessation of suction of the device with one hand, while the users other hand is free to secure a lesion or immobilize a palpable mass. In bone marrow procedures, an aspirating force can be applied to assist in retrieving an osteoporotic bone marrow specimen, while the physician is free to withdraw the needle.

Finally, the simplicity of the invention lends itself to production as a disposable item, eliminating the need for costly and time-consuming sterilization, maintenance and storage.

In addition to solving the prior art problems already mentioned, the present invention has the advantage that the technique for using it is considerably faster than the prior art techniques, thereby reducing the danger of accidental organ laceration and attendant internal bleeding. This in turn reduces the chance of post-biopsy patient complications such as pneumothorax, hemoptysis and interstitial bleeding.

The speed with which the present invention may be used can also help minimize artifaction of the sample due to contact with the air. Samples may be expelled directly onto slides or into sample containers promptly after removal from the patient. For example, with fluid aspirated during fine needle aspiration, this may be done simply by once again forcing the plunger into the syringe after having obtained a desired sample, thereby expelling the aspirated fluid. It is also possible to expel soft tissue samples in the same fashion. It should also be noted that after the initial flushing procedure in a soft tissue biopsy, it is often necessary to remove the needle from the syringe, draw saline solution into the syringe, replace the needle and then expel the tissue. Each of these steps is simplified when the structure of the present invention is used.

It will be appreciated that the present invention provides an improved aspirating device, controllable by a single hand and useful for performing subcutaneous biopsy of fluid, soft tissues and bone marrow. The simplicity of the present invention is itself evidence of nonobviousness when viewed in the light of the many more complicated devices invented over the years in attempts to solve the same problem.

BRIEF DESCRIPTION OF THE DRAWINGS

FIG. 1 is a perspective view of a device embodying the principles of the present invention.

FIG. 2 is a cross-sectional view along the line 2—2 in FIG. 1.

DETAILED DESCRIPTION OF THE INVENTION

Figure 3:
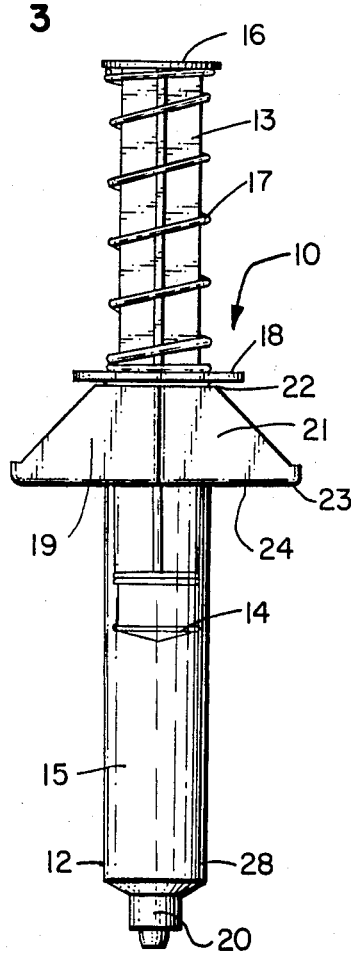
FIG. 3 is a perspective view of the device embodying the principles of the present invention including an alternate finger grip member.

A preferred embodiment of the present invention will be explained with reference to FIGS. 1 through 7, in which like elements are designated with like reference numbers. In a preferred embodiment an aspirating device 10, similar to a medical hypodermic syringe, is provided and includes a syringe barrel 12; a finger grip member 21; a plunger 13 and spring means, such as a spring 17, for biasing the plunger 13 outwardly from the barrel 12 after the plunger 13 has been advanced in the barrel 12. The aspirating device 10 can be provided with a thin-walled hollow needle 11, the lumen of which opens through a transparent hub 20 into the barrel 12 of the aspirating device 10.

The barrel 12 of the aspirating device 10 has an exterior wall, an interior wall, a first or distal end 28 and a second or proximal end 18. The walls and ends define a hollow interior space having a predetermined volume. Further, the barrel 12 includes a hub 20 and opening through the hub 20 and barrel 12 at the distal end 28.

The plunger 13 extends within and external to the barrel 12 and is operative therein. Particularly, the plunger 13 has a first end inside the barrel 12 and a second end external to the barrel 12. The plunger 13 has a gasket 14 at its first end inside the barrel 12 which interacts with the walls of the barrel 12 to effectively create a space 15 inside the barrel 12. The gasket 14 consists of material different than the barrel, such as rubber, so that the plunger first end is sealingly received within the barrel. The plunger 13 variably controls the volume and pressure within the barrel space 15. When plunger 13 is positioned in the barrel 12 the only opening into the barrel interior is provided by the opening at the distal end 28 of the barrel. When needle 11 is attached at hub 20, the only opening into the barrel 12 is provided by the lumen of needle 11. At the second end of the plunger 13, which is outside the barrel 12, the plunger 13 is provided with a pressure plate 16. Preferably, the pressure plate 16 is rounded so as to be more comfortably pressed against by the user's palm.

In the preferred embodiment, the spring means includes a spring 17 which surrounds the plunger portion external to the barrel 12. The spring 17 extends along the plunger 13 between the pressure plate 16 and the barrel proximal end 18. The spring 17 biases the plunger 13 outwardly from the proximal end of barrel 12 after the plunger 13 has been advanced into the barrel 12 toward the distal end 28 thereof. It will be appreciated that the coil spring 17 shown in the drawings may be replaced with a different spring-like material. For example, the plunger 13 could be encompassed by a compressible polymeric resin which will bias the plunger 13 out of the syringe barrel 12 when it is compressed.

Figure 4:
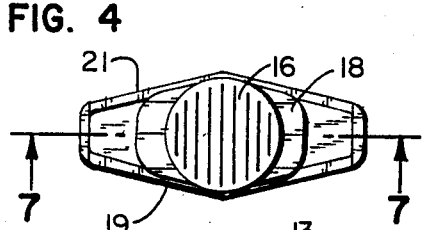
FIG. 4 is a top view of the finger grip member of the present invention as shown in FIG. 3.

An important feature of the present invention is a finger grip member 21 surrounding the exterior wall of the barrel 12. The finger grip member 21 is positioned along the barrel 12 substantially adjacent the proximal end 18 of the barrel 12. The finger grip member 21 includes a collar portion 22 and a pair of flange portions 19. Each of the flange portions 19 extend outwardly from the collar portion 22 a distance sufficient to provide support for at least one finger of a user's hand. As seen in FIG. 1, the flange portions 19 may be in the form of arcuate extensions projecting outwardly from the collar 22. Alternatively, a preferred embodiment of the finger grip member 21 includes flange portions 19 having a substantially flat surface 24 against which the user's fingers can be positioned, as best seen in FIG. 3. Further, as shown in FIGS. 3-5, the flange portions 19 may be provided with slightly rounded end tips 23 which provide additional safety and comfort for the user during use of the device 10.

It will be appreciated that the collar 22 of finger grip member 21 includes an interior surface which engages the exterior wall of the barrel 12 and is slidable thereon. Specifically, the collar portion 22 can slidably and frictionally engage the exterior wall of the barrel 12, thereby providing a finger grip member which can be positioned along the barrel 12 without the need of retaining devices such as pins or rivets or adhesives, such as glues or expoxies.

Figure 7:
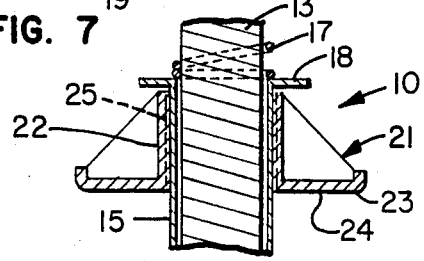
FIG. 7 is a cross-sectional view taken generally along the line 7—7 in FIG. 4.
Figure 5:
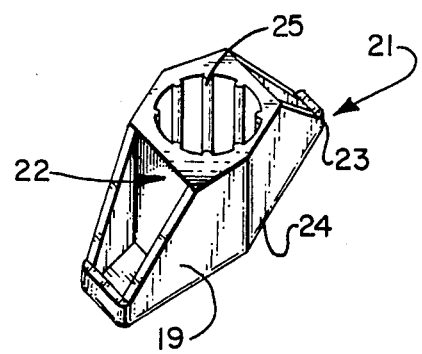
FIG. 5 is a perspective view of finger grip member of the present invention as shown in FIG. 3.

As seen in FIGS. 5 and 7 the interior surface of the collar 22 can include a plurality of ribs 25 positioned around the interior surface of the collar 22. The ribs 25 are arranged to run along the longitudinal axis of the collar 22 so that the ribs 25 align with the longitudinal axis of the barrel 12 when the finger grip member 21 is positioned thereon. The ribs 25 compress the barrel wall, thereby providing for tighter frictional engagement between the finger grip member 21 and the external wall of the barrel 12.

As seen in FIGS. 1 through 4 the proximal end 18 can terminate at a rim projecting outwardly from the barrel 12. The rim provides a stop to limit movement of the finger grip member 21 at the proximal end 18.

It will further be appreciated that the barrel 12, plunger 13 and finger grip member 21 can be plastic and entirely disposable. The finger grip member 21 is preferably of polypropylene. Additionally, the hub portion 20 of the barrel 12, as well as syringe barrel itself can be transparent to facilitate viewing of fluids and specimens therein.

Figure 6:
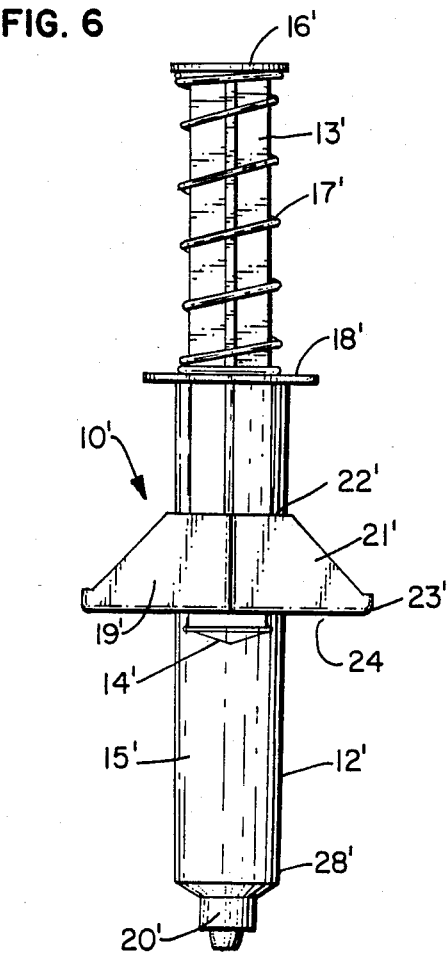
FIG. 6 is a perspective view of an alternate embodiment of the present invention.

In FIG. 6, an alternate embodiment of the aspirating device 10' is shown. As shown in FIG. 6, the syringe barrel 12' is tapered from the proximal end 18' to the distal end 28'. It will be appreciated that by increasing the taper of the barrel 12' movement of the finger grip member 21' toward the proximal end 18' of the barrel 12' is correspondingly limited. Thus, the desired position of the finger grips member 21' along the barrel 12' can be set by the amount of taper to the barrel 12' enabling the finger grip member 21' to be optimally positioned along the barrel 12' for a particular user's grip or specific type of aspiration procedure. When the finger grip member 21' is provided with ribs 25', the ribs 25' increasingly compress the barrel wall as the finger grip member 21' is moved toward the proximal end 18', thereby allowing the finger grip member 21' to be adjustably positioned along the tapered barrel 12'.

The aspirating device 10 of the present invention can be used in conjunction with a needle. In a preferred embodiment, a hollow needle 11 having a first end and a second is attached to the hub 20 as seen in FIGS. 1 and 2. More particularly, the first end of the needle 11 is sealingly engaged and detachably connected to the distal end 28 of the barrel 12 at the hub 20, thereby providing fluid communication between the lumen of the needle 11 and the interior of the barrel 12.

To perform a soft tissue biopsy, the aspiration device 10 is used in conjunction with needle 11 attached to hub 20. The fingers of a user's hand are placed below the finger grip member 21 with the palm of the same hand being placed on the pressure plate 16. The plunger 13 is then forced into the barrel 12 by compressing the spring 17 thereby reducing the space 15. The needle 11 is then placed in a saline solution and the grip eased slightly so that the spring 17 will force the plunger 13 outwardly from the barrel 12. This in turn causes an expansion of the space 15. The consequent reduced or negative pressure in the space 15 draws the saline solution into the barrel 12 of the aspirating device 10. The grip pressure is then increased to halt suction. After patient preparation, the needle 11 is then inserted through an incision into the patient up to the tissue to be sampled and the plunger 13 is again pressed into the barrel 12 by the user, drawing the finger grip member 21 toward the palm of the hand, thereby forcing the saline solution out through the needle 11. This flushes the needle of any interstitial fluid or material that may have entered the central hollow space or lumen of the needle 11. The needle 11 is then quickly advanced into the tissue and the grip eased at the rate necessary to create the desired suction through the needle 11 to sever the specimen. When a suitable sample has been drawn into the needle, suction is again halted by a slight reapplication of the gripping pressure on the plunger 13 and finger grip member 21. After obtaining the sample, the needle 11 is then removed from the tissue and the specimen expelled from the needle for histologic or cytologic examination.

As mentioned previously, the aspirating device 10 can be provided with a transparent hub 20 connecting the needle 11 to the barrel 12. In performing fine needle aspirations the transparent hub 20 is preferred in order that the withdrawn sample may be seen and the suction terminated before the sample enters the barrel 12.

In fine needle aspiration a fluid is removed from a subcutaneous mass such as a nodule or palpable mass. It is necessary for the physician to secure the lesion or immobilize the mass with the fingers of one hand, while the needle is introduced through the skin. Specifically, to perform fine needle aspiration, the hand is placed on the device 10 in the same fashion as for a soft tissue biopsy. The grip is compressed and the needle 11 inserted through the skin into a mass to be sampled. Once the needle is in the lesion, the grip is eased, providing suction to aspirate the fluid to be sampled. The grip may be reapplied and again eased to halt and reapply suction, respectively, as the needle 11 is redirected and reinserted until sufficient fluid is aspirated and visible in the transparent hub 20. As soon as aspirated material is visible in the transparent hub 20, suction is stopped by the reapplication of gripping pressure, thereby stopping the outward movement of the plunger 13. The plunger 13 is then compressed slightly to neutralize any negative pressure in the barrel 12. The needle 11 is then withdrawn from the patient and the aspirated fluid promptly expelled directly onto a slide by forcing the plunger 13 downwardly into the barrel 12. It is important that the user be able to control the application and cessation of suction, since artifaction will occur if the fluid is aspirated into the syringe barrel and exposed to air. The speed of performing fine needle aspiration with the present device 10 minimizes possible artifaction due to exposure to air.

The aspirating device 10 of the present invention may also be used to obtain a bone marrow biopsy specimen. A common bone condition of the elderly is osteoporosis, a malady which makes the retrieval of a bone marrow specimen extremely difficult. In a bone marrow procedure, a large needle is introduced into the posterior illiac crest. When an osteoporotic specimen is encountered, the sample is severed and located inside the needle lumen. Because of the composition of the specimen, it is often impossible to retrieve the specimen. However, by compressing the grip on the present invention to build up partial vacuum, attaching it to the proximal end of the biopsy needle and then releasing the grip, a constant suction may be maintained, freeing the physicians hand to remove the needle.

To perform a bone marrow biopsy with the aspirating device 10 of the present invention, the hub 20 should include a locking mechanism, such as a Luer Lok ® brand locking mechanism, capable of being attached to a bone marrow biopsy needle. When the bone marrow needle is sufficiently inserted with a stylet, the stylet is then removed and the needle advanced into a marrow cavity. The spring 17 around the plunger 13 of the aspirating device 10 is compressed in the same fashion as for a soft tissue biopsy. The aspirating device 10 is then attached to the bone marrow needle and the grip released to provide a suction force to obtain a specimen. With the aspirating device 10 applying suction, one or both hands may then be used to withdraw the bone marrow needle from the patient using the same back and forth rotating technique employed to insert it.

When the operator wishes to apply suction while inserting or withdrawing the needle 11, any of the procedures above may be altered by changing the points in the procedure at which the grip is eased and tightened. The amount of suction may be varied by changing the rate at which the grip is eased or released.

It shall be understood that the above-described embodiments of the present invention are merely exemplary, and that the spirit and scope of the present invention are not limited thereto, being defined by the claims set forth below.

What is claimed is:

1. An aspirating device, comprising:
   a syringe barrel having an exterior wall, an interior wall, a distal end and a a proximal end, said walls and said ends defining a hollow interior space having a predetermined volume, said distal end having an opening and a hub, said distal end opening extending through said hub, said proximal end terminating at an outwardly projecting rim;
   a finger grip member surrounding said exterior wall of said barrel and positioned along said barrel substantially adjacent said proximal end thereof, said finger grip member including a collar portion having an interior surface engaging said exterior wall of said barrel and a pair of flange portions extending outwardly from said collar portion, each of said flanges extending outwardly from said exterior wall of said barrel a distance sufficient to provide support for at least one finger of a user and having a substantially flat surface terminating at a rounded end tip, said finger grip member being slidable along said barrel and said interior surface of said collar frictionally engaging said exterior wall of said barrel substantially adjacent said outwardly projecting rim of said proxiaml rim of said proximal end of said barrel, whereby said frictional engagement is such that it compresses said barrel wall to allow selective placement and retention of said finger grip member along said barrel;
   a plunger operative in said barrel, said plunger extending both within said barrel interior space and external to said barrel proximal end and having a first end sealingly received inside said barrel and a second end outside said barrel, said plunger being movable within said barrel interior space inwardly toward said distal end and outwardly away from said distal end, thereby varying the volume of and pressure within said barrel interior space, said plunger including a pressure plate at said second end; and
   spring means surrounding said plunger portion external to said barrel and extending along said plunger between said pressure plate and said barrel proximal end, said spring means biasing said plunger outwardly from said barrel after said plunger has been advanced in said barrel toward said distal end thereof.

2. An aspirating device in accordance with claim 1 wherein said spring means is a coil spring.

3. An aspirating device in accordance with claim 1 wherein said finger grip member is plastic.

4. An aspirating device in accordance with claim 1 wherein said pressure plate is rounded.

5. An aspirating device in accordance with claim 1 further comprising a hollow needle having a first end opening into said barrel at said barrel's distal end and a second end extending outwardly from said barrel distal end, said needle being sealingly engaged to said distal end of said barrel at said hub thereby allowing fluid communication between said needle and said barrel.

6. An aspirating device in accordance with claim 1 wherein said finger grip member includes a plurality of ribs on said interior surface of said collar, said ribs running along the longitudinal axis of said collar.

7. A disposable aspirating device, comprising:
   a plastic syringe barrel having an exterior wall, an interior wall, a distal end and a proximal end, said walls and said ends defining a hollow interior space having a predetermined volume, said distal end having an opening and a hub, said distal end opening extending through said hub, said proximal end terminating at an outwardly projecting rim;
   a plastic finger grip member surrounding said exterior wall of said barrel and positioned along said barrel substantially adjacent said proximal end thereof, said finger grip member including a collar having an interior surface engaging said exterior wall of said barrel and a pair of flange portions extending outwardly from said collar portion, each of said flanges extending outwardly from said exterior wall of said barrel a distance sufficient to provide support for at least one finger of a user and having a substantially flat surface terminating at a rounded end tip, said interior surface of said collar slidably and frictionally engaging said exterior wall of said barrel substantially adjacent outwardly projecting rim of said proximal end of said barrel, whereby said frictional engagement is such that it compresses said barrel wall to allow selective placement and retention of said finger grip member along said barrel;
   a plastic plunger operative in said barrel, said plunger extending both within said barrel interior space and external to said barrel proximal end and having a first end sealingly received inside said barrel and a second end outside said barrel, said plunger being movable within said barrel interior space inwardly toward said distal end and outwardly away from said distal end, thereby varying the volume of and pressure within said barrel interior space, said plunger including a pressure plate at said second end; and a spring surrounding said plunger portion external to said barrel, said spring extending along said plunger between said pressure plate and said barrel proximal end, said spring biasing said plunger outwardly from said barrel after said plunger has been advanced in said barrel toward the distal end thereof.

8. An aspirating device in accordance with claim 7 wherein said finger grip member includes a plurality of ribs on said interior surface of said collar, said ribs running along the longitudinal axis of said collar.

* * * * *